(12) United States Patent
Gross et al.

(10) Patent No.: US 9,572,816 B2
(45) Date of Patent: Feb. 21, 2017

(54) METHOD OF TREATMENT OF DISEASE

(71) Applicant: TECHNION RESEARCH AND DEVELOPMENT FOUNDATION LTD., Haifa (IL)

(72) Inventors: Zeev Gross, Petach Tikva (IL); Adi Haber, Haifa (IL); Itzchak Angel, Nes Ziona (IL)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 14/438,413

(22) PCT Filed: Oct. 24, 2013

(86) PCT No.: PCT/IL2013/050863
§ 371 (c)(1),
(2) Date: Apr. 24, 2015

(87) PCT Pub. No.: WO2014/064697
PCT Pub. Date: May 1, 2014

(65) Prior Publication Data
US 2015/0290214 A1    Oct. 15, 2015

Related U.S. Application Data

(60) Provisional application No. 61/718,441, filed on Oct. 25, 2012, provisional application No. 61/718,387, filed on Oct. 25, 2012.

(51) Int. Cl.
| | |
|---|---|
| *A61K 31/555* | (2006.01) |
| *A61K 31/409* | (2006.01) |
| *A61K 38/41* | (2006.01) |
| *C07D 487/22* | (2006.01) |

(52) U.S. Cl.
CPC ........... *A61K 31/555* (2013.01); *A61K 31/409* (2013.01); *A61K 38/41* (2013.01); *C07D 487/22* (2013.01)

(58) Field of Classification Search
None
See application file for complete search history.

(56) References Cited

FOREIGN PATENT DOCUMENTS

| | | |
|---|---|---|
| WO | 00/19993 | 4/2000 |
| WO | 00/27379 | 5/2000 |
| WO | WO-0075122 A2 | 12/2000 |
| WO | 2004/052227 | 6/2004 |
| WO | 2005/097123 | 10/2005 |
| WO | WO-2009027965 A1 | 3/2009 |
| WO | WO-2009095923 A3 | 8/2009 |

OTHER PUBLICATIONS

Sugawara, et al., Curr. Eye Res., 29:11 (2004).*
Kanamori, et al., J. Neurochem., 114:488 (2010).*
Zoya Okun et al; Manganese Corroles Prevent Intracellular Nitration and Subsequent Death of Insulin-Producing Cells; ACS Chemical Biology; vol. 4, No. 11; Nov. 20, 2009.
Maria-Magdalena Catrinescu et al; Superoxide signaling and cell death in retinal ganglion cell axotomy; Effects of metallocorroles; Experimental Eye Research; vol. 97, No. 1; Apr. 1, 2012;.
M.A. Abdelsaid et al; Early Intervention of Tyrosine Nitration Prevents Vaso-Obliteration and Neovascularization in Ischemic Retinopathy; Journal of Pharmacology and Experimental Therapeutics; vol. 332; No. 1' Jan. 1, 2010.
Pal Pacher et al; Role of Nitrosative Stress and Peroxynitrite in the Pathogenesis of Diabetic Complications. Emerging New Therapeutical Strategies; Current Medicinal Chemistry; vol. 12, No. 3; Feb. 1, 2005.
Adi Haber et al; Combating diabetes complications by 1-Fe, a corrole-based catalytic antioxidant; Journal of Diabetes and Its Complications; vol. 27, No. 4; Jul. 1, 2013.
Partial Supplementary European Search Report dated May 10, 2016 for corresponding European application 13849439.8.
Extended European Search Report dated Aug. 26, 2016 for corresponding European application 13849439.8.

* cited by examiner

*Primary Examiner* — Michael Barker
(74) *Attorney, Agent, or Firm* — A.C. Entis-IP Ltd.

(57) ABSTRACT

An embodiment of the invention provides a use of an effective amount of a transition metal complex of a corrole, an optically active isomer thereof, or a pharmaceutically acceptable salt thereof for treating a disease of the eye and/or the kidney in a subject suffering from diabetes. An embodiment of the invention further provides a use of a transition metal complex of a corrole, an optically active isomer thereof, or a pharmaceutically acceptable salt thereof for lowering serum glucose and serum triglyceride levels in a subject suffering from diabetes.

20 Claims, 4 Drawing Sheets

METHOD OF TREATMENT OF DISEASE

RELATED APPLICATIONS

The present application claims the benefit under 35 U.S.C. 119(e) of U.S. Provisional Applications 61/718,387 and 61/728,441 both filed on Oct. 25, 2012, the disclosures of which are incorporated herein by reference.

TECHNICAL FIELD

Embodiments of the invention relate to compositions and methods for the treatment of diseases primarily of the eye and the kidney.

BACKGROUND

Diabetes is a chronic metabolic disorder characterized by hyperglycemia (elevated blood glucose levels) that leads to the development of vascular complications, especially in small blood vessels of the eye, kidney, and peripheral nerves. These tissues are especially vulnerable to hyperglycemic conditions, since the cells constructing these tissues may uptake glucose in an uncontrolled fashion.

A cataract is a disease of the lens of the eye in which a clouding obstructs the passage of light, causing vision loss and potentially blindness. Cataract prevalence is higher in patients suffering from diabetes than in non-diabetic population. Surgical extraction of cataract is the only cure known today. In addition to cataracts, diabetes has been linked with other diseases of the eye including glaucoma, retinopathy, macular edema and retinal detachment.

Chronic kidney disease (CKD) is a disease associated with high morbidity and mortality. CKD is characterized by a slow progressive loss of renal function, chronic inflammation, oxidative stress, vascular remodeling and scarring of kidney tissue. Diabetic nephropathy (DN) is a leading cause of CKD. In some instances, DN can lead to end stage renal disease (ESRD) in which a patient's kidneys cease to function and the patient requires kidney transplant or dialysis in order to survive.

SUMMARY

An embodiment of the invention provides a method for treating a disease of the eye in a subject comprising administering an effective amount of a transition metal complex of a corrole, an optically active isomer thereof, or a pharmaceutically acceptable salt thereof.

In an embodiment of the invention, the disease of the eye is selected from the group consisting of: cataracts, glaucoma, retinopathy, macular edema and retinal detachment.

An embodiment of the invention provides a method for treating CKD in a subject comprising administering an effective amount of a transition metal complex of a corrole, an optically active isomer thereof, or a pharmaceutically acceptable salt thereof.

According to an embodiment of the invention, methods of treating a disease of the eye or CKD are performed on a patient having diabetes.

Corroles are organic molecules having a contracted porphyrin ring comprising nineteen carbon atoms and 4 nitrogen atoms, and are capable of binding transition metals. Transition metal complexes of corroles were found to have an antioxidant effect. The iron(III) complex of a corrole whose structural formula is depicted below, also known as 1-Fe, is a potent catalytic antioxidant.

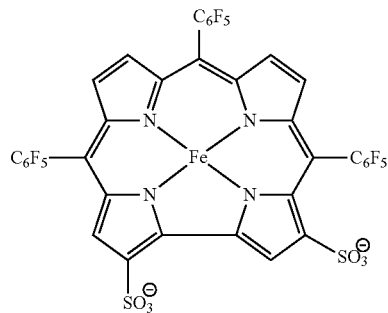

Without being bound by theory, it is suggested that one of the mechanisms in which diabetes may cause cataract and other diseases of the eye or CKD is through overproduction of reactive oxygen species and reactive nitrogen species which negatively impact the vascular tissue through oxidative stress. In addition, it has been suggested that high glucose levels in diabetic patients leads to high sorbitol concentrations in the eye, thereby damaging the lens and potentially causing cataract formation. The antioxidant corroles, according to embodiments of the invention, have shown effect in treatment of diseases of the eye and the kidney.

Although oxidative stress has previously been implicated in cataracts and in particular in diabetic cataracts, some previous attempts to use antioxidant for treating cataracts have failed. For example, it has been reported that based on a number of clinical studies involving the antioxidants vitamin E, vitamin C and beta-carotene showed no significant effect on the development of cataract. (Meyer & Sekundo, 2005)

Oxidative stress has also previously been implicated in CKD and in particular in DN, however, some previous attempts to use antioxidant in models of DN have failed. For example, the known antioxidant curcumin, although administered in levels sufficient to be present in the kidney, was not successful in treating DN in a rat model (Ma, et al., 2010).

In contrast with the clinical studies involving vitamin E, vitamin C, curcumin and beta carotene, corrole compounds according to embodiments of the invention were successful in treating and preventing damage to the eye and kidney in rat models.

According to some embodiments of the invention, methods are provided for lowering blood glucose levels in a subject in need thereof comprising administering an effective amount of a transition metal complex of a corrole, an optically active isomer thereof, or a pharmaceutically acceptable salt thereof. According to embodiments of the invention, the subject is a diabetic patient suffering from type 1 or type 2 diabetes.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph.

DETAILED DESCRIPTION

Figure 1A:
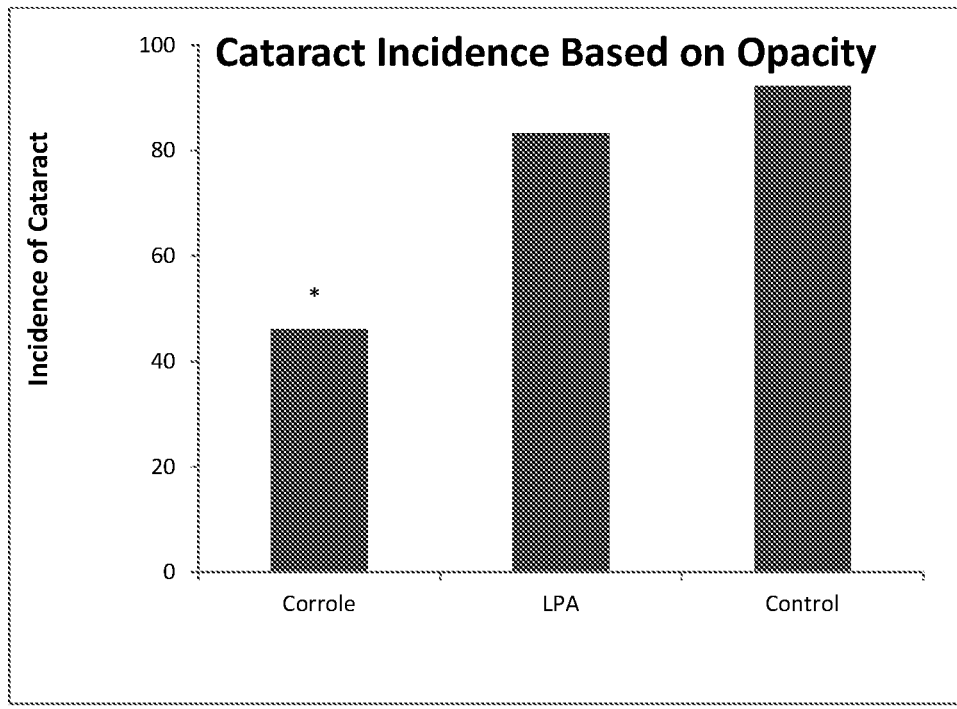
FIG. 1A shows a bar chart depicting incidence of cataract based on measurement of lens opacity in a rat model in which rats were inflicted with a cataract-like disease state and administered either a corrole, an antioxidant alpha lipoic acid (LPA) or a vehicle (control)

Corroles, and in particular 1-Fe, have been shown by the inventors to improve measures of cataract and kidney function in rats in models in which diabetes was induced in rats using streptozotocin (STZ). The advantageous effect of corroles formulated with a vehicle was evident in this model when compared to rats in a control group treated with a vehicle alone without an active ingredient and even when compared to rats treated with a known antioxidant, alpha lipoic acid (LPA).

It is suggested in accordance with an embodiment of the invention, methods of treatment and/or prevention of disease of the eye and/or of the kidney in a subject comprising administering a pharmaceutical composition comprising an effective amount of a transition metal complex of a corrole, an optically active isomer thereof, or a pharmaceutically acceptable salt thereof. In an embodiment of the invention, the subject suffers from type 1 diabetes. In an embodiment the subject suffers from type 2 diabetes. In an embodiment of the invention, the subject suffers from diabetic cataract. In an embodiment of the invention, the subject suffers from DN.

Pharmaceutical compositions comprising corroles have been disclosed in U.S. Pat. No. 6,730,666, incorporated herein by reference. Methods of manufacture of corroles are described in U.S. Pat. No. 6,541,628, incorporated herein by reference.

In an embodiment of the invention the transition metal complex of a corrole has the formula,

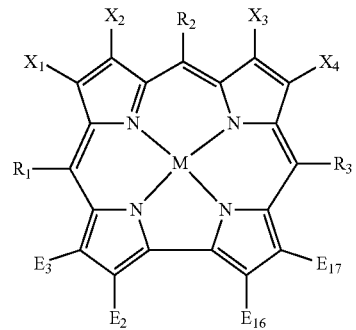

where $R_1$, $R_2$ and $R_3$ are each independently a carbocyclic aryl ring or a heterocyclic aryl ring, each ring comprising 5 or 6 atoms. M is a transition metal selected from the group consisting of Mn, Fe, Ru, Co, V, Cr, and Cu and $X_1$, $X_2$, $X_3$ and $X_4$ are each independently H or a halogen. $E_2$, $E_3$, $E_{17}$ and $E_{18}$ are each independently H, halogen, $SO_2Cl$, $SO_3H$, $SO_2NR_4R_5$, $CO_2H$, $CO_2R$, $COCl$, $CONR_4R_5$, $CHO$, $CH=C(CO_2H)_2$, $CH=C(CN)CO_2H)$, or $NO_2$. R is alkyl or aryl and $R_4$ and $R_5$ are each independently H, alkyl, aryl or together with the N atom to which they are attached form a saturated 5-6 membered ring. Optionally the ring comprises an additional heteroatom selected from the group consisting of O, S and N. Optionally alkyl is C1-C4 alkyl and aryl is C6-C12 aryl.

In an embodiment of the invention, in which the transition metal is Fe, $R_1$, $R_2$ and $R_3$ are each pentafluorophenyl; both $E_2$ and $E_{17}$ are $SO_3H$; $E_3$ and $E_{18}$ are H, and $X_1$, $X_2$, $X_3$, and $X_4$ are each H.

In an embodiment of the invention, in which the transition metal is Fe; $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H.

In an embodiment of the invention, in which the transition metal is Mn; $R_1$, $R_2$ and $R_3$ are each pentafluorophenyl; $E_2$ and $E_{17}$ are $SO_3H$; $X_1$, $X_2$, $X_3$ and $X_4$ are each H; and $E_3$ and $E_{18}$ are H.

In an embodiment of the invention, in which the transition metal is Mn; $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H.

In an embodiment of the invention, the transition metal complex of a corrole, or an optically active isomer thereof or a pharmaceutically acceptable salt thereof is provided via oral, rectal, vaginal, topical, nasal, ophthalmic, transdermal, subcutaneous, intramuscular, intraperitoneal or intravenous administration.

The pharmaceutical compositions according to an embodiment of the invention are conveniently presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe.

The compositions of the present invention are generally administered in the form of a pharmaceutical composition comprising at least one active component together with a pharmaceutically acceptable carrier or diluent.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the components of this invention can be combined with various sweetening agents, flavoring agents, coloring agents, emulsifying agents and/or suspending agents, as well as such diluents as water, ethanol, propylene glycol, glycerin and various like combinations thereof.

The compositions according to embodiments of this invention may also be administered in a controlled release formulation such as a slow release or a fast release formulation. Such controlled release dosage composition may be prepared using methods well known to those skilled in the art.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

Pharmaceutical compositions according to embodiments of the invention may contain an active amount of 0.1%-95% of the corrole(s), preferably 1%-70%.

In an embodiment of the invention, the daily dosage of the transition metal complex of a corrole, an optically active isomer thereof or a pharmaceutically acceptable salt thereof is between 0.1 milligram (mg) and 1500 mg (expressed in terms of active corrole equivalent in the case of a salt).

Some embodiments of the invention relate to treatments as monotherapy, in which a corrole is a sole active pharmaceutical agent used to treat a disease. Some embodiments of the invention relate to combination therapies in which a corrole is used in combination with another active pharmaceutical agent to treat a disease. "In combination with" refers to both drugs being substantially effective in the body at a same time. Both drugs can be administered substantially at the same time, or both drugs can be administered at different times but have effect on the body at the same time.

Treatment for eye disease in accordance with an embodiment of the invention is illustrated by the following example of an experiment in which eye damage is induced in rats.

Example 1

Eye Damage in a Rat Model of STZ-Induced Diabetes

Eight to ten-week old male Sprague Dawley rats were used in the model. Rat handling was performed according to guidelines of the National Institute of Health (NIH) and the Association for Assessment and Accreditation of Laboratory Animal Care (AAALAC). Diabetes was induced by intraperitoneal injection of 50 mg/kilogram (mg/kg) STZ (in 0.1 molar citrate buffer), which is a dose generally sufficient to destroy all insulin-producing beta cells and induce a diabetic disease-like state. Two weeks later, glucose levels were measured and rats displaying a level lower than 200 mg per deciliter (dL) were excluded from the study. The remaining rats were randomly divided into 3 groups (according to body weight and serum glucose levels): a control group, a corrole group and an LPA group. Each group received a 7-week course of treatment. The control group (13 rats) received water with no active ingredient. The corrole group (14 rats) received 20 mg/kg/day of the corrole designated 1-Fe. 1-Fe was synthesized using the procedure described in Mahammed et al. (Mahammed, Goldberg, & Gross, 2001). The LPA group (13 rats) received 50 mg/kg/day LPA. LPA was formulated for administration by dissolving in 1 millimolar sodium hydroxide (NaOH) which was then brought to a pH of 7.5. Treatments during weekdays were provided by oral gavage (administration to the lower oesophagus) of 10 milliliters (ml) of solution, while during the weekends the antioxidants were supplied to the rats' drinking water (concentration of antioxidants was adjusted based on 200 mL of drinking water for each rat for each day).

Body weight was measured throughout the experiment for all rats and is shown in table 1 below.

TABLE 1

| | Before disease induction (all groups) | Start of treatment (all groups) 2 weeks after induction | After 7 weeks of treatment | | |
|---|---|---|---|---|---|
| | | | Control Group | Corrole Group | LPA group |
| Body weight (grams) | 276 ± 11 | 276 ± 23 | 266 ± 8 | 283 ± 12 | 0 ± 6 |

While healthy rats constantly gain weight, the induction of disease caused complete arrest of weight gain after 2 weeks, followed by significant weight loss during the treatment phase for the control and LPA groups. On the other hand, the corrole treated group gained weight, and at the end of treatment the average weight of the group was significantly higher relative to the other two groups. This indicates that overall health of rats in the corrole group was better than the health of the rats in the LPA group.

Cataract was evaluated a day before termination of the trial in live rats by measurement of opacities of the rat's lenses of each eye with a slit-lamp biomicroscope following the application of tropicamide eye drops. A 0 to 4 scoring system was used to score cataract level according to the following scale: score 0: clear lens; score 1: swollen fibers and subcapsular opacities observed; score 2: nuclear cataract in lens and swollen fibers in lens cortex; score 3: strong nuclear cataract with perinuclear area opacity in lens; score 4: total opacity of lens.

A rat having a score in at least one eye of 1 or higher was considered to have developed a cataract. The percentage of rats in each group having a cataract (cataract incidence) as determined by opacity measurements for each group is shown in FIG. 1A. As shown in the figure, almost all of the rats in the control group developed cataract. The percentage of rats in the corrole group that developed a cataract was less than 50% (p=0.015), significantly lower than the control group. LPA did not have a significant effect on the cataract incidence.

Figure 1B:
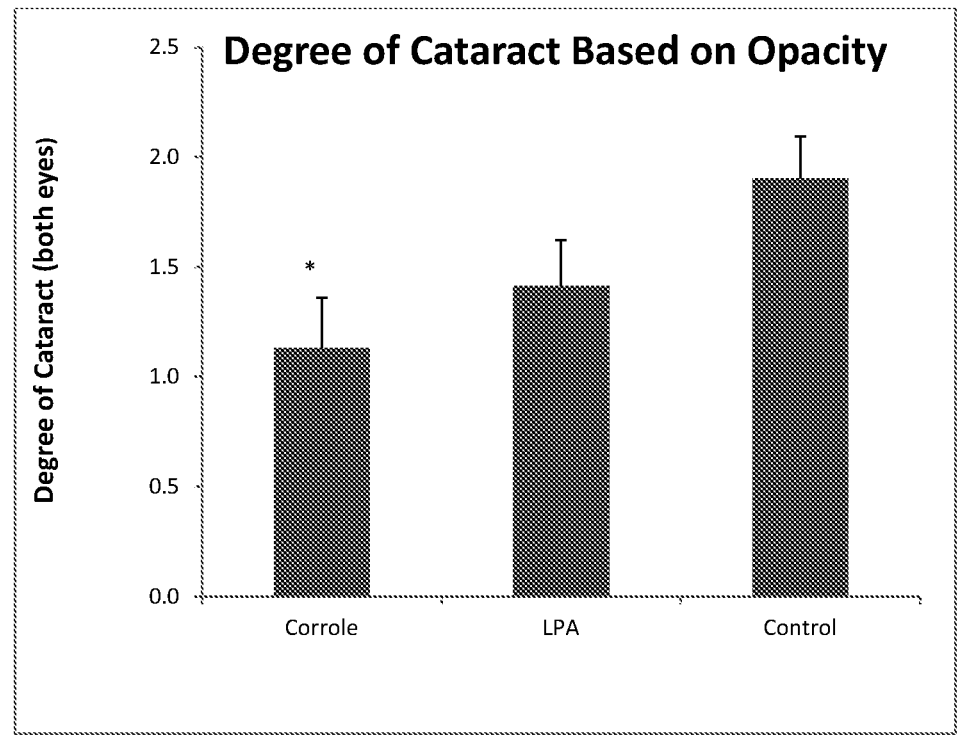
FIG. 1B shows a bar chart depicting degree of cataract based on measurement of lens opacity in both eyes of rats in a rat model in which rats were inflicted with a cataract-like disease state and administered either a corrole, LPA or a vehicle (control)

The degree of cataract for both eyes as determined by averaging each group's cataract scoring of both eyes of each rat as determined by opacity measurement is shown in FIG. 1B. As shown in the figure, the degree of cataract was significantly lower in the corrole group by 42% relative to the control group (p=0.014.) LPA induced a 28% reduction in degree of cataract (p=0.1.)

Figure 1C:
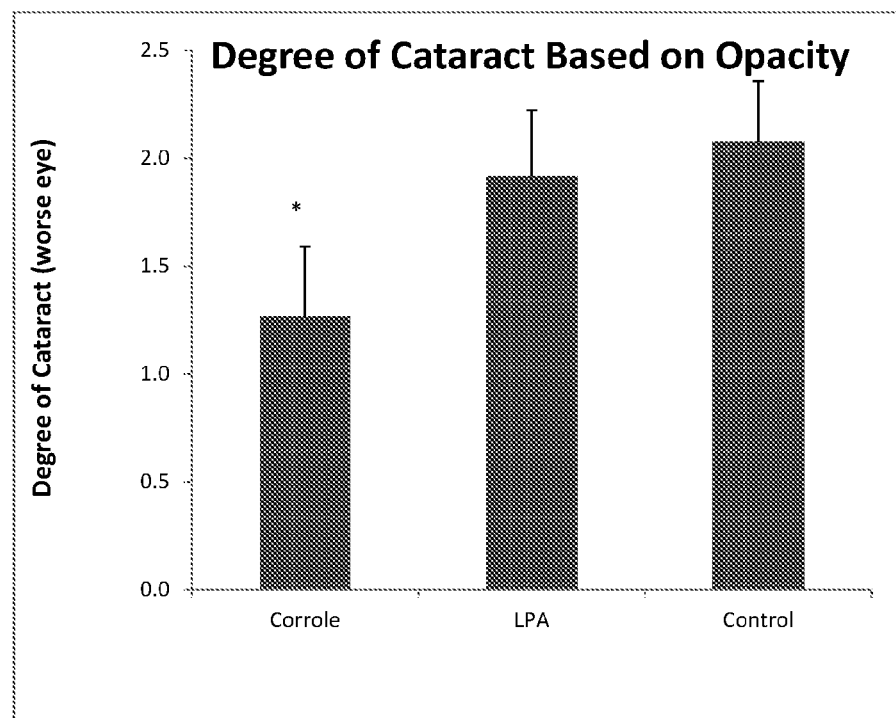
FIG. 1C shows a bar chart depicting degree of cataract based on measurement of lens opacity in rats' worse eye in a rat model in which rats were inflicted with a cataract-like disease state and administered either a corrole, LPA or a vehicle (control)

As cataract may develop at a different rate in each of the animals' eyes, the degree of cataract for the rats' worse eye was evaluated. The degree of cataract for the rats' worse eye was determined by averaging each group's cataract scoring of each animal's worse eye as determined by opacity measurement, and is shown in FIG. 1C. As shown in the figure, the degree of cataract in the worse eye of rats in the corrole group was decreased by 39% relative to that of the control group (p=0.072). On the other hand, the reduction in degree of cataract in worse eye for the LPA group was not significantly reduced relative to the control group.

The development of cataractous damage was further evaluated by histological examination. Lens nerve fiber degradation was estimated by Hematoxylin and eosin (H&E) staining of the lenses collected after sacrifice upon study termination. A scale of 0 to 4 was used to score nerve fiber degradation based on amount of Morganian globules in the lenses.

A rat having a score in at least one eye of 1 or higher was considered to have suffered a cataractous damage. The percentage of rats in each group having a cataractous damage (cataract damage incidence) as determined by histological examination of lenses for each group is shown in FIG. 1D.

Figure 1D:
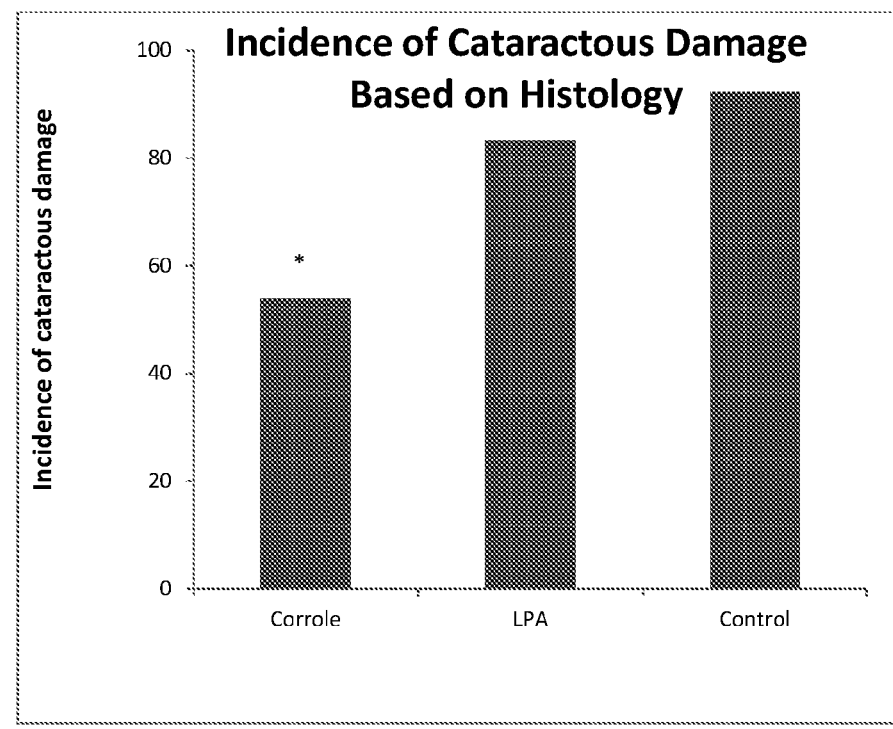
FIG. 1D shows a bar chart depicting incidence of cataractous damage based on histological analysis following a rat model in which rats were inflicted with a cataract-like disease state and administered either a corrole. LPA or a vehicle (control)

As can be seen in FIG. 1D, histological examination of lenses confirmed that cataract damage incidence is reduced in the corrole group relative to the control group (p=0.073). The effect of treatment in the LPA group, on the other hand, was minimal.

Figure 1E:
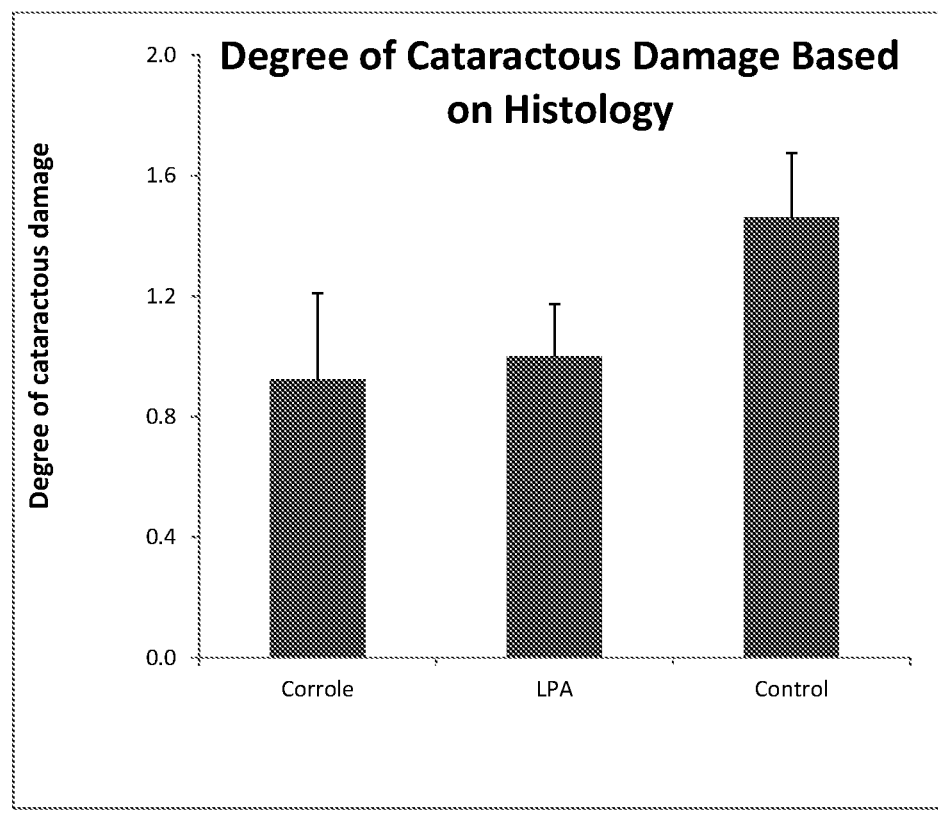
FIG. 1E shows a bar chart depicting degree of cataractous damage based on histological analysis of lenses of both eyes of rats following a rat model in which rats were inflicted with a cataract-like disease state and administered either a corrole, LPA or a vehicle (control)

The degree of cataractous damage for both eyes as determined by averaging each group's cataract scoring of both eyes of each rat as determined by histological examination is shown in FIG. 1E. As shown in the figure, the degree of cataractous damage was lower in the corrole group by 37% relative to the control group. LPA induced a 32% reduction in degree of cataractous damage.

These results indicate that corroles are highly beneficial in the treatment of the effect of STZ induced disease on the eye, in particular in treating a cataract. The results of this model indicates that corroles, including 1-Fe, even when administered systemically, are available in eye tissue and are viable agents for treatment and/or prevention of eye diseases, especially in patients suffering from diabetic-related eye diseases.

Example 2A

Kidney Damage in a Rat Model of STZ-Induced Diabetes

A rat model was performed as in example 1, but rather than testing for eye damage, blood testing was used to test for creatinine levels. Creatinine is a compound present in mammalian serum and urine which is formed by the breakdown of muscle and is removed from the body through the kidneys. In mammals with renal malfunction, the flow rate of filtered fluid through the kidney is reduced, and the creatinine clearance from the body is thereby impaired. Creatinine clearance rate (CrCl), an established measure for evaluating renal function, was calculated for rats in all groups of the trial by dividing the amount of creatinine in the urine (mg/minute) by its concentration in the serum (mg/ml).

CrCl was measured: a) before induction of diabetes; b) 2 weeks later when the treatment commenced; and c) following 7 weeks of treatment (9 weeks from STZ injection). Average CrCl values for each group are shown in Table 2.

TABLE 2

| | Before disease induction (all groups) | Start of treatment (all groups) | After 7 weeks of treatment | | |
|---|---|---|---|---|---|
| | | | Control Group | Corrole Group | LPA group |
| CrCl (ml/min) | 1.35 ± 0.35 | 0.60 ± 0.12 | 0.72 ± 0.10 | 1.24 ± 0.16 | 1.36 ± 0.28 |

Induction of disease caused a very significant reduction in creatinine clearance, with no additional change following 7 weeks of treatment in the control group. However, both corrole and LPA significantly ameliorated creatinine clearance, bringing it almost back to the level before the induction of diabetes. There was an increase of 72% (p=0.027) for the corrole 1-Fe and 89% (p=0.078) for LPA relative to the control group.

In summary, CrCl was reduced by more than 50% upon diabetes induction, and CrCl remained practically unchanged after 7 weeks in the control group. On the other hand, the groups treated with corrole and LPA for 7 weeks displayed CrCl similar to that seen before the induction of diabetes (Table 2). This indicates that corroles almost completely treated the effect of STZ induced disease on the kidneys.

This model indicates that corroles, including 1-Fe, are viable agents for treatment and/or prevention of CKD. Corroles may be used for the treatment of CKD, especially in patients suffering from diabetic nephropathy.

Example 2B

Effect of corroles on DN development may be further shown in a model in *Psammony Obesus*, a sand rat that develops diet induced diabetes when fed standard laboratory chow. It is suggested that corroles may have an effect in the model in reducing CKD.

Example 3A

Reduction of Blood Glucose Levels Using Corroles

Apolipoprotein (apo) E3-Leiden is a mutation found in humans which is associated with a form of familial dysbetalipproteinemia. Transgenic mice were generated using a construct isolated from the ApoE*3-Leiden proband. The transgenic mice develop elevated levels of plasma cholesterol and triglycerides on a regular diet relative to non-transgenic mice.

Figure 2:
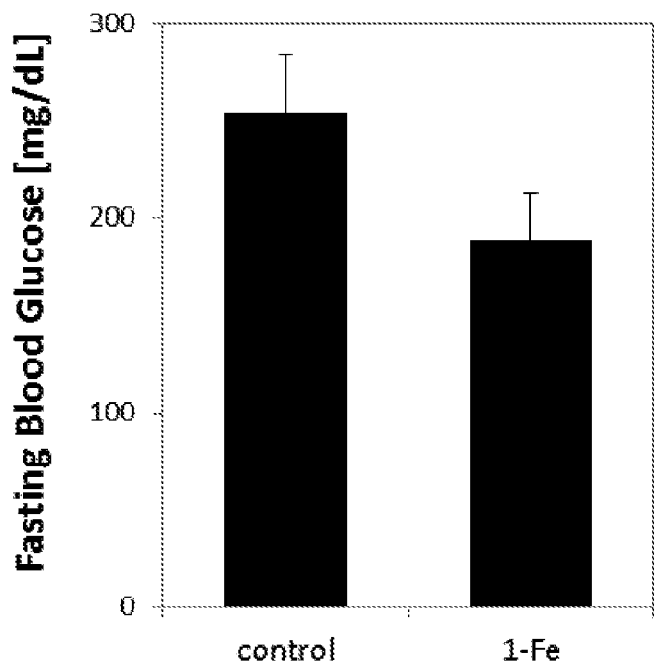
FIG. 2 shows a bar chart depicting differences in fasting blood glucose level (expressed in milligrams per deciliter, mg/dl) in mice receiving corroles relative to mice receiving control.

Twelve 9-week old female apoE*3-Leiden transgenic mice received a high-fat high-cholesterol diet for 5 weeks, after which they were allocated into 2 groups of 6 mice each having similar cholesterol levels. The mice then received a 5-week treatment of either vehicle (0.5% carboxymethyl cellulose solution) or 10 mg/kg/day 1-Fe. Treatment during the 5 consecutive weekdays was via oral gavage of 8 mL/kg, while during the weekends the additives were supplied to the animals' drinking water (concentration adjusted according to 4 mL/mouse/day). The level of fasting blood glucose was determined for all mice at the end of the treatment period. Mice treated by 1-Fe displayed a 25% decrease in blood glucose relative to untreated mice. A bar graph depicting differences in fasting blood glucose level (expressed in milligrams per deciliter, mg/dl) in mice receiving corroles relative to mice receiving control is shown in FIG. 2.

As mentioned above, elevated blood glucose level can lead to development of vascular complications, especially in small blood vessels of the eye, kidney, and peripheral nerves, as cells constructing these tissues may uptake glucose in an uncontrolled fashion. Corroles, according to embodiments of the inventions, may be used in lowering blood glucose levels, thereby curing and/or preventing diseases of the eye and/or kidneys in diabetic patients.

Example 3B

Reduction of Triglyceride Levels in Animals Using Corroles

Figure 3:
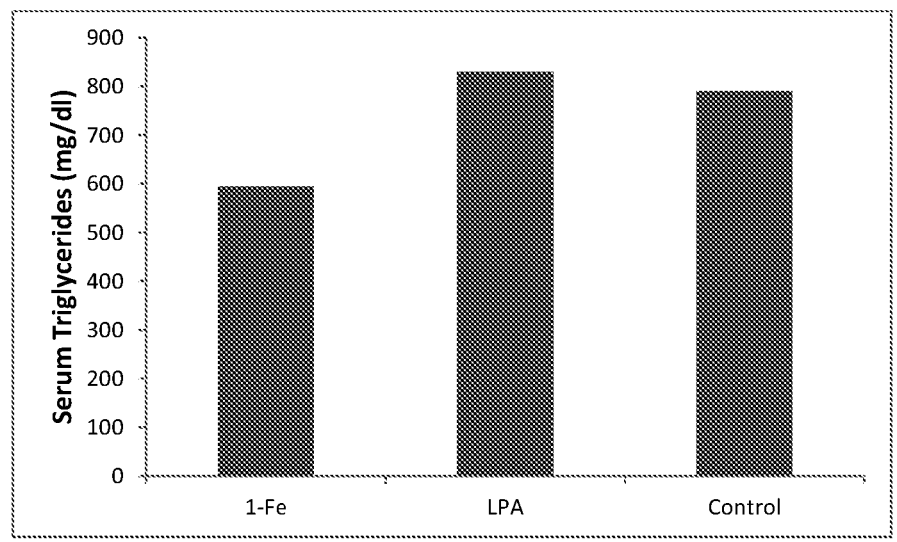
FIG. 3 shows a bar chart depicting differences in triglyceride level in mice receiving corroles relative to mice receiving LPA or a vehicle (control).

An experiment was performed as in example 2A with the exception that serum triglyceride levels were determined. As shown in FIG. 3, the corrole 1-Fe lowers triglyceride levels by 25% relative to the control group which was administered vehicle alone. In addition, triglyceride levels were lowered by corroles relative to the antioxidant LPA.

High triglyceride levels in diabetic patients may be indicative of development of Type 2 diabetes. Reducing triglyceride levels using corroles according to embodiments of the invention may prevent development of diabetic complications such as CKD and diseases of the eye.

There is further provided, in accordance with an embodiment of the invention, a method for treating or preventing a disease of the eye or of the kidney in a subject suffering from diabetes comprising administering to the subject a medicament comprising a transition metal complex of a corrole, an optically active isomer thereof or a pharmaceutically acceptable salt thereof. Optionally, the disease of the eye is cataracts, glaucoma, retinopathy, macular edema or retinal detachment. Optionally, the disease of the kidney is chronic kidney disease, diabetic nephropathy or end stage renal disease. Optionally, the transition metal complex of a corrole has the formula,

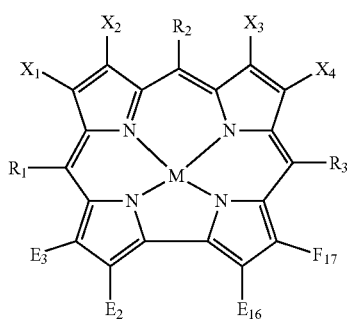

where $R_1$, $R_2$ and $R_3$ are each independently a carbocyclic aryl ring or a heterocyclic aryl ring, each ring comprising 5 or 6 atoms. M is a transition metal selected from the group consisting of Mn, Fe, Ru, Co, V, Cr, and Cu and $X_1$, $X_2$, $X_3$ and $X_4$ are each independently H or a halogen. $E_2$, $E_3$, $E_{17}$ and $E_{18}$ are each independently H, halogen, $SO_2Cl$, $SO_3H$, $SO_2NR_4R_5$, $CO_2H$, $CO_2R$, $COCl$, $CONR_4R_5$, $CHO$, $CH{=}C(CO_2H)_2$, $CH{=}C(CN)CO_2H)$, or $NO_2$. R is alkyl or aryl and $R_4$ and $R_5$ are each independently H, alkyl, aryl or together with the N atom to which they are attached form a saturated 5-6 membered ring, the ring comprising 1, 2 or 3 heteroatoms selected from the group consisting of O, S and N. Optionally, alkyl is C1-C4 alkyl and aryl is C6-C12 aryl. Optionally, M is Fe; $R_1$, $R_2$ and $R_3$ are each pentafluorophenyl; both $E_2$ and $E_{17}$ are $SO_3H$; $E_3$ and $E_{18}$ are H, and $X_1$, $X_2$, $X_3$, and $X_4$ are each H. Optionally, M is Fe; $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H. Optionally, M is Mn; $R_1$, $R_2$ and $R_3$ are each pentafluorophenyl; $E_2$ and $E_{17}$ are $SO_3H$; $X_1$, $X_2$, $X_3$ and $X_4$ are each H; and $E_3$ and $E_{18}$ are H. Optionally, M is Mn; $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H. Optionally, the transition metal complex of a corrole is 1-Fe. Optionally, the medicament is configured for oral, rectal, vaginal, topical, nasal, ophthalmic, transdermal, subcutaneous, intramuscular, intraperitoneal or intravenous administration. Optionally, the medicament comprises between 0.1 mg and 1500 mg of a corrole. Optionally, the medicament is configured to be administered to a patient once daily, twice daily or three times daily. Optionally, the medicament is configured to be administered to a patient once weekly or twice weekly. Optionally, the subject suffers from type 1 diabetes. Optionally, the subject suffers from type 2 diabetes.

There is further provided, in accordance with an embodiment of the invention a method for lowering serum glucose level in a subject comprising administering to the subject a medicament comprising a transition metal complex of a corrole, an optically active isomer thereof or a pharmaceutically acceptable salt thereof. Optionally, the subject suffers from diabetes.

There is further provided, in accordance with an embodiment of the invention a method for lowering serum triglyceride level in a subject comprising administering to the subject a medicament comprising a transition metal complex of a corrole, an optically active isomer thereof or a pharmaceutically acceptable salt thereof. Optionally, the subject suffers from diabetes.

There is further provided, in accordance with an embodiment of the invention a pharmaceutical composition for the treatment of a disease of the eye or of the kidney in a subject suffering from diabetes comprising a transition metal complex of a corrole, an optically active isomer thereof or a pharmaceutically acceptable salt thereof.

There is further provided, in accordance with an embodiment of the invention a use of a transition metal complex of a corrole, an optically active isomer thereof or a pharmaceutically acceptable salt thereof for the manufacture of a medicament for treating or preventing a disease of the eye or of the kidney in a subject suffering from diabetes.

There is further provided, in accordance with an embodiment of the invention a pharmaceutical composition for lowering scrum glucose level or for lowering serum triglyceride level in a subject comprising a transition metal complex of a corrole, an optically active isomer thereof or a pharmaceutically acceptable salt thereof.

There is further provided, in accordance with an embodiment of the invention a use of a transition metal complex of a corrole, an optically active isomer thereof or a pharmaceutically acceptable salt thereof for the manufacture of a medicament for lowering serum glucose level or for lowering serum triglyceride level in a subject.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

BIBLIOGRAPHY

Ma, J, Phillips, L., Wang, Y., Dai, T., Lapage, J., Nataragan, R., et al. (2010). Curcumin activates the p38MPAK-HSP25 pathway. *BMC Complementary and Alternative Medicine,* 10 (67), 1-17.

Mahammed, A., Goldberg, I., & Gross, Z. (2001). Highly Selective Chlorosulfonation of Tris(pentafluorophenyl) corrole as a Synthetic Tool for the Preparation of Amphiphilic Corroles and Metal Complexes of Planar Chirality. *Org. Lett.,* 3, 3443-6.

Meyer, C., & Sekundo, W. (2005). Nutritional Supplementation to Prevent Cataract Formation. *Dev. Opthamol.,* 38, 103-119.

The invention claimed is:

1. A method of treating a disease of the eye or of the kidney in a subject suffering from diabetes comprising: administering to the subject a transition metal complex of a corrole, an optically active isomer thereof or a pharmaceutically acceptable salt thereof.

2. The method according to claim 1 wherein the disease of the eye is cataracts, glaucoma, retinopathy, macular edema or retinal detachment.

3. The method according to claim 1 wherein the disease of the kidney is chronic kidney disease, diabetic nephropathy or end stage renal disease.

4. The method according to claim 1, wherein the transition metal complex of a corrole has the formula:

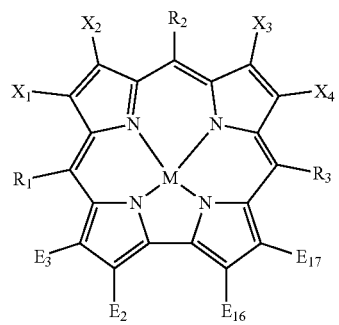

where $R_1$, $R_2$ and $R_3$ are each independently a carbocyclic aryl ring or a heterocyclic aryl ring, each ring comprising 5 or 6 atoms, M is a transition metal selected from the group consisting of Mn, Fe, Ru, Co, V, Cr, and Cu and $X_1$, $X_2$, $X_3$ and $X_4$ are each independently H or a halogen, $E_2$, $E_3$, $E_{17}$ and $E_{18}$ are each independently H, halogen, $SO_2Cl$, $SO_3H$, $SO_2NR_4R_5$, $CO_2H$, $CO_2R$, $COCl$, $CONR_4R_5$, $CHO$, $CH=C(CO_2H)_2$, $CH=C(CN)CO_2H)$, or $NO_2$, R is an alkyl or aryl and $R_4$ and $R_5$ are each independently H, alkyl, aryl or together with the N atom to which they are attached form a saturated 5-6 membered ring, the ring comprising 1, 2 or 3 heteroatoms selected from the group consisting of O, S and N.

5. The method according to claim 4, wherein the alkyl is C1-C4 alkyl and aryl is C6-C12 aryl.

6. The method according to claim 4, wherein M is Fe; $R_1$, $R_2$ and $R_3$ are each pentafluorophenyl; both $E_2$ and $E_{17}$ are $SO_3H$; $E_3$ and $E_{18}$ are H, and $X_1$, $X_2$, $X_3$ and $X_4$ are each H.

7. The method according to claim 4, wherein M is Fe; $R_1$, $R_2$, and $R_3$ are each 4-nitrophenyl; $E_2$ and $E_{17}$ are $SO_3H$; $X_1$, $X_2$, $X_3$, and $X_4$ are each H; and $E_3$ and $E_{18}$ are H.

8. The method according to claim 4, wherein M is Mn; $R_1$, $R_2$, and $R_3$ are each pentafluorophenyl; $E_2$ and $E_{17}$ are $SO_3H$; $X_1$, $X_2$, $X_3$, and $X_4$ are each H; and $E_3$ and $E_{18}$ are H.

9. The method according to claim 4, wherein M is Mn; $R_1$, $R_2$, and $R_3$ are each 4-nitrophenyl; $E_2$ and $E_{17}$ are $SO_3H$; $X_1$, $X_2$, $X_3$, and $X_4$ are each H; and $E_3$ and $E_{18}$ are H.

10. The method according to claim 1 wherein the transition metal complex of a corrole is 1-Fe.

11. The method according to claim 1 wherein the transition metal complex of a corrole is configured for oral, rectal, vaginal, topical, nasal, ophthalmic, transdermal, subcutaneous, intramuscular, intraperitoneal or intravenous administration.

12. The method according to claim 1 wherein the transition metal complex of a corrole comprises between 0.1 mg and 1500 mg of a corrole.

13. The method according to claim 12 wherein the medicament is configured to be administered to a patient once daily, twice daily or three times daily.

14. The method according to claim 12 wherein the transition metal complex of a corrole is configured to be administered to a patient once weekly or twice weekly.

15. The method according to claim 1 wherein the subject suffers from type 1 diabetes.

16. The method according to claim 1 wherein the subject suffers from type 2 diabetes.

17. A method of lowering serum glucose level in a subject suffering from a disease of the eye or of the kidney comprising: administering to the subject a transition metal complex of a corrole, an optically active isomer thereof or a pharmaceutically acceptable salt thereof.

18. The method according to claim 17, wherein the subject suffers from diabetes.

19. A method for lowering serum triglyceride level in a subject suffering from a disease of the eye or of the kidney, comprising administering to the subject a transition metal complex of a corrole, an optically active isomer thereof or a pharmaceutically acceptable salt thereof.

20. The method according to claim 19, wherein the subject suffers from diabetes.

* * * * *